United States Patent [19]

Hokama

[11] 4,022,610
[45] May 10, 1977

[54] HERBICIDAL MIXED SALTS OF MAGNESIUM

[75] Inventor: Takeo Hokama, Chicago, Ill.

[73] Assignee: Velsicol Chemical Corporation, Chicago, Ill.

[22] Filed: May 16, 1975

[21] Appl. No.: 578,058

Related U.S. Application Data

[62] Division of Ser. No. 406,512, Oct. 15, 1973, Pat. No. 3,910,974.

[52] U.S. Cl. ................................................. 71/115
[51] Int. Cl.² ........................................... A01N 9/24
[58] Field of Search ..................................... 71/115

[56] References Cited

UNITED STATES PATENTS

| | | | |
|---|---|---|---|
| 3,012,870 | 12/1961 | Richter | 71/115 |
| 3,081,162 | 3/1963 | Tishler | 71/115 |
| 3,248,208 | 4/1966 | Weil | 71/115 |

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

This invention discloses mixed salts of magnesium having the empirical formula

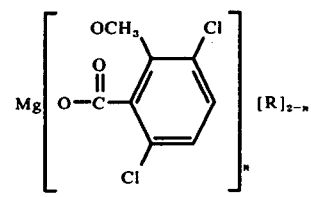

wherein R is an organic acid radical of 7 to 20 carbon atoms; and *n* has an average value of from 0.5 to 1.5. The compounds of the above description are useful as herbicides.

2 Claims, No Drawings

HERBICIDAL MIXED SALTS OF MAGNESIUM

This application is a division of copending application Ser. No. 406,512, filed Oct. 15, 1973 now U.S. Pat. No. 3,910,974, issued Oct. 7, 1975.

This invention relates to new compositions of matter and more specifically relates to new mixed salts of magnesium having the empirical formula

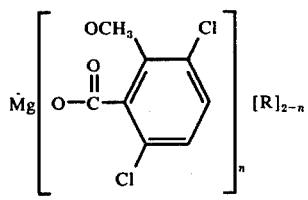

wherein R is an organic acid radical having from 7 to 20 carbon atoms; and $n$ has an average value of from 0.5 to 1.5.

The compounds of the present invention are useful as herbicides and possess the unexpected property of resisting leaching in the soil.

Weeds often grow new the soil surface whereas many beneficial plants have their roots deeper in the ground. Thus, to avoid injury to the beneficial plants which may be partially sensitive to a herbicide, it is desirable to minimize leaching or downward movement of the herbicide in the soil. Furthermore, a basis for the pre-emergence action of herbicides is often the difference in depth between the planted crop seeds and the weed seeds on the surface of the soil. Crop seeds are generally planted 1 to 3 inches deep and are somewhat protected from chemicals applied to the soil surface, while weed seeds generally germinate only in the top one-forth inch of the soil and are thus subject to a much higher concentration of the chemical. To maintain this dfference in concentration of the chemical, it is desirable to have a herbicide which is resistant to leaching in the soil. The compounds of the present invention resist leaching to a high degree.

The compounds of the present invention can be prepared by reacting a magnesium salt of an organic acid having from 7 to 20 carbon atoms with an appropriate amount of 2-methoxy-3,6-dichlorobenzoic acid according to the following equation:

$$Mg(R)_2 + nC_6H_2OCH_3Cl_2CO_2H \rightarrow$$

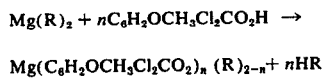

wherein R and $n$ are as heretofore described. This reaction can be effected by combining the reactants in an inert organic reaction medium such as benzene, toluene, or xylene and heating the reaction mixture at reflux for a period of from about 1 to about 24 hours. After this time the reaction mixture can be stripped of solvent under reduced pressure to yield the desired product.

The mixed magnesium salts of the present invention can also be prepared by reacting an inorganic water soluble magnesium salt such as magnesium nitrate, magnesium sulfate, magnesium chloride and the like with appropriate amounts of an alkali metal salt of 2-methoxy-3,6-dichlorobenzoic acid and an alkali metal salt of an organic acid having from 7 to 20 carbon atoms according to the following exemplary equation:

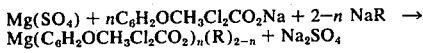

wherein R and $n$ as heretofore described. This reaction can be effected by adding an aqueous solution of the inorganic magnesium salt to the appropriate stoichiometric mixture of the salts of the organic acids in an aqueous reaction medium. The resulting mixture can be heated at temperatures of from about 60 to about 95° C for a period of up to several hours. After this time, the desired product can be recovered by filtration and can be used as such or can be further purified by conventional means.

The sodium salts of the organic acids can also be prepared in situ by using a strong basic reaction medium such as an aqueous alkali metal hydroxide.

As previously indicated, the R group is an organic acid radical having from 7 to 20 carbon atoms. Suitable acids which can be used in the form of their alkali metal salts such as the sodium or potassium salt to prepare the compounds of this invention and obtain the desired R group are aliphatic acids, oenanthic acid, caprylic acid, pelargonic acid, capric acid, neodecanoic acid, undecanoic acid, lauric acid, tridecanoic acid, myristic acid, pentadecanoic acid, palmitic acid, margaric acid and stearic acid; aromatic acids such as benzoic acid, toluic acid, ethylbenzoic acid, t-butylbenzoic acid, phthalic acid, isophthalic acid, 3-chlorobenzoic acid, 4-chlorobenzoic acid, 3,4-dichlorobenzoic acid, 2,4-dichlorobenzoic acid, 2,4,6-trichlorobenzoic acid, 2,4,5-trichlorobenzoic acid, 2-methyl-4-chlorobenzoic acid, phenylacetic acid, 3-chlorophenylacetic acid, 4-chlorophenylacetic acid, 2,4-dichlorophenylacetic acid, 3,4-dichlorophenylacetic acid, 2,4,5-trichlorophenylacetic acid, phenoxyacetic acid, 2,4-dichlorophenoxyacetic acid, 3,4-dichlorophenoxyacetic acid, 2,4,5-trichlorophenoxyacetic acid and the like.

The manner in which the compounds of the present invention can be prepared is more specifically illustrated in the following examples.

EXAMPLE 1

Preparation of a Mixed salt of Magnesium, 2-Methoxy-3,6-dichlorobenzoic Acid and Stearic Acid of the Empirical Formula $Mg(C_6H_2OCH_3Cl_2CO_2)$ $(C_{18}H_{35}O_2)$ Magnesium stearate, $Mg(C_{18}H_{35}O_2)_2$ (29.6 grams; 0.05 mole) 2-methoxy-3,6-dichlorobenzoic acid (11.0 grams; 0.05 mole) and benzene (200 ml.) were charged into a glass reaction flask equipped with a mechanical stirrer, thermometer and reflux condenser. The reaction mixture was heated at reflux for a period of about 1 hour. After this time, the reaction mixture was cooled to room temperature to yield a solution of the desired product having the empirical formula $Mg(C_6H_2OCH_3Cl_2CO_2)$ $(C_{18}H_{35}O_2)$.

EXAMPLE 2

Preparation of a Mixed Salt of Magnesium, 2-Methoxy-3,6-dichlorobenzoic Acid and Stearic Acid of the Empirical Formula $Mg(C_6H_2OCH_3Cl_2CO_2)_{0.5}$ $(C_{18}H_{35}O_2)_{1.5}$ Magnesium stearate, $Mg(C_{18}H_{35}O_2)_2$ (88.8 grams; 0.15 mole), 2-methoxy-3,6-dichlorobenzoic acid (11 grams; 0.05 mole) and benzene (300 ml.) are charged into a glass reaction flask equipped with a mechanical stirrer, thermometer and reflux condenser. The reaction mixture is heated at a temperature of about 80° C until solution occurs. After this time, the reaction mixture is stripped of solvent under reduced pressure to yield the desired product as a solid having the empirical formula $Mg(C_6H_2OCH_3Cl_2CO_2)_{0.5}$ $(C_{18}H_{35}O_2)_{1.5}$.

EXAMPLE 3

Preparation of a Mixed Salt of Magnesium, 2-Methoxy-3,6-dichlorobenzoic Acid and Stearic Acid of the Empirical Formula $Mg(C_6H_2OCH_3Cl_2CO_2)_{1.5}$ $(C_{18}H_{35}O_2)_{0.5}$ A solution of a 2-methoxy-3,6-dichlorobenzoic acid (33.15 grams; 0.15 mole) in benzene (250 ml.) is placed into a glass beaker and magnesium stearate, $Mg(C_{18}H_{35}O_2)_2$ (59.1 grams; 0.10 mole) is added thereto. The mixture is heated on a steam bath with stirring until gellation occurs. The gelled product is then stripped of solvent to yield a solid product. This product is further dried in a vacuum oven at 100° C under aspirator pressure. A portion of the resulting product (10 grams) is then charged with xylene (50 grams) into a flask equipped with a reflux condenser. The mixture is then heated at reflux to yield a solution of the desired product of the empirical formula $Mg(C_6H_2OCH_3Cl_2CO_2)_{1.5}$ $(C_{18}H_{35}O_2)_{0.5}$.

EXAMPLE 4

Preparation of a Mixed Salt of Magnesium, 2-Methoxy-3,6-dichlorobenzoic Acid and Stearic Acid of the Empirical Formula $Mg(C_6H_2OCH_3Cl_2CO_2)$ $(C_{18}H_{35}O_2)$ 2-Methoxy-3,6-dichlorobenzoic acid (11.05 grams; 0.05 mole) and stearic acid (14.22 grams; 0.05 mole) are added to a solution of sodium hydroxide (4 grams; 0.10 mole) in water (50 ml.). The mixture is heated to melt the stearic acid thereby forming a heterogeneous solution. This solution is then added to a solution of magnesium chloride (4.76 grams; 0.05 mole) in water (100 ml.) with vigorous stirring. Stirring is continued for a period of about 60 minutes to yield a solid product, This porduct is recovered by filtration, is washed with water and is dried under vacuum at 100° C. Five grams of this product is then dissolved in xylene to yield a solution of the desired product of the empirical formula $Mg(C_6H_2OCH_3Cl_2CO_2)$ $(C_{18}H_{38}O_2)$.

EXAMPLE 5

Preparation of a Mixed Salt of Magnesium, 2-Methoxy-3,6-dichlorobenzoic Acid and Benzoic Acid of the Empirical Formula $Mg(C_6H_2OCH_3Cl_2CO_2)$ $(C_6H_5CO_2)$ 2-Methoxy-3,6-dichlorobenzoic acid (33.15 grams; 887% assay 0.15 mole), benzoic acid (18.3 grams; 0.15 mole), sodium hydroxide (12.0 grams; 0.3 mole) and water (300 ml.) are charged into a glass reaction vessel equipped with a mechanical stirrer and reflux condenser. The mixture is heated to 90° C and a solution of magnesium chloride (14.28 grams; 0.15 mole) in water (100 ml.) is added with stirring. The mixture is re-heated to 90° C and is then allowed to cool to room temperature. The cooled mixture is then filtered to recover the desired product as a powdered solid having the empirical formula $Mg(C_6H_2OCH_3Cl_2CO_2)$ $(C_6H_5CO_2)$.

EXAMPLE 6

Preparation of a Mixed Salt of Magnesium, 2-Methoxy-3,6-dichlorobenzoic Acid and Octanoic Acid of the Empirical Formula $Mg(C_6H_2OCH_3Cl_2CO_2)$ $(C_8H_{15}O_2)$ 2-Methoxy-3,6-dichlorobenzoic acid (33.15 grams; 87% assay; 0.15 mole), octanoic acid (21.6 grams; 0.15 mole), sodium hydroxide (12.0 grams; 0.3 mole) and water are charged into a reaction vessel equipped with thermometer and mechanical stirrer. The mixture is heated to a temperature of about 90° C and a solution of magnesium chloride (14.28 grams; 0.15 mole) in water (100 ml.) is added thereto. The mixture is re-heated to a temperature of about 80° C and is then allowed to cool to room temperature. The solid formed is recovered by filtration; washed with water and dried. The dried product is then refluxed in xylene to yield a solution of the desired product having the empirical formula $Mg(C_2H_2OCH_3Cl_2CO_2)$ $(C_8H_{15}O_2)$.

EXAMPLE 7

Preparation of a Mixed Salt of Magnesium, 2-Methoxy-3,6-dichlorobenzoic Acid and Toluic Acid of the Empirical Formula $Mg(C_6H_2OCH_3Cl_2CO_2)$ $(C_6H_4CH_3CO_2)$ 2-Methoxy-3,6-dichlorobenzoic acid (33.15 grams; 85% assay; 0.15 mole), toluic acid (0.15 mole), sodium hydroxide (12.0 grams; 0.3 mole) and water (250 ml.) are charged into a glass reaction vessel equipped with a mechanical stirrer and thermometer. The mixture is heated to a temperature of about 85° C and a solution of magnesium chloride (0.15 mole) in water (100 ml.) is added thereto. The mixture is then heated at about 90° C for a period of about 60 minutes with continued stirring. After this time the reaction mixture is cooled to room temperature and is filtered to recover solid product. This solid is then washed with water and is dried to yield the desired product of the empirical formula $Mg-(C_6H_2OCH_3Cl_2CO_2)$ $(C_6H_4CH_3CO_2)$.

EXAMPLE 8

Preparation of a Mixed Salt of Magnesium, 2-Methoxy-3,6-dichlorobenzoic Acid and Oenanthic Acid of the Empirical Formula $Mc(C_6H_2OCH_3Cl_2CO_2)$ $(C_6H_{13}CO_2)$ 2-Methoxy-3,6 -dichlorobenzoic acid (0.15 mole), oenanthic acid (0.15 mole), sodium hydroxide (12.0 grams) and water (250 ml.) are charged into a glass reaction vessel equipped with a mechanical stirrer and thermometer. The mixture is heated to a temperature of about 90° C and a solution of magnesium chloride (0.15 mole) in water (100 ml.) is added thereto. The mixture is then heated to a temperature of about 90° C for a period of about 45 minutes with continued stirring. After this time, the reaction mixture is cooled to room temperature and is filtered to recover solid product. This solid is then washed with water and is dried to yield the desired product of the empirical formula $Mg(C_6H_2OCH_3Cl_2CO_2)$ $(C_6H_{13}CO_2)$.

EXAMPLE 9

Preparation of a Mixed Salt of Magnesium, 2-Methoxy-3,6-dichlorobenzoic Acid and Caprylic Acid of the Empirical Formula $Mg(C_6H_2OCH_3Cl_2CO_2)$ $(C_7H_{15}CO_2)$ 2-Methoxy-3,6-dichlorobenzoic acid (0.15 mole), caprylic acid (0.15 mole), sodium hydroxide (12.0 grams) and water (250 ml.) are charged into a glass reaction vessel equipped with a mechanical stirrer and thermometer. The mixture is heated to a temperature of about 85° C and a solution of magnesium chloride (0.15 mole) in water (100 ml.) is added thereto. The mixture is then heated at about 85° C for a period of about 60 minutes with continued stirring. After this time the reaction mixture is cooled to room temperature and is filtered to recover solid product. This solid is then washed with water and is dried to yield the desired product of the empirical formula $Mg(C_6H_2OCH_3Cl_2Co_2)$ $(C_7H_{15}Co_2)$.

EXAMPLE 10

Preparation of a Mixed Salt of Magnesium, 2-Methoxy-3,6-dichlorobenzoic Acid and t-Butylbenzoic Acid of the Empirical Formula $Mc(C_6H_2OCH_3Cl_2CO_2)$ $(C_6H_4C_4H_9CO_2)$ 2-Methoxy-3,6-dichlorobenzoic acid (0.11 mole), t-butylbenzoic acid (0.11 mole), sodium hydroxide (8.8 grams) and water (250 ml.) are charged into a glass reaction vessel equipped with a mechanical stirrer and thermometer. The mixture is heated to a temperature of about 80° C and a solution of magnesium chloride (0.11 mole) in water (100 ml.) is added thereto. The mixture is then heated at about 80° C for a period of about 90 minutes with continued stirring. After this time, the reaction mixture is cooled to room temperature and is filtered to recover solid product. This solid is then washed with water and is dried to yield the desired product of the empirical formula $Mg(C_6H_2OCH_3Cl_2CO_2)$ $(C_6H_4C_4H_9CO_2)$.

EXAMPLE 11

Preparation of a Mixed Salt of Magnesium, 2-Methoxy-3,6-dichlorobenzoic Acid and 2,4-Dichlorophenoxyacetic Acid of the Empirical Formula $Mg(C_6H_2OCH_3Cl_2CO_2)$ $(C_6H_3Cl_2OCH_2CO_2)$ 2-Methoxy-3,6-dichlorobenzoic acid (33.15 grams; 85% assay; 0.15 mole), 2,4-dichlorophenoxyacetic acid (33 grams; 0.15 mole), sodium hydroxide (12 grams) and water (250 ml.) are charged into a reaction vessel equipped with thermometer and mechanical stirrer. The mixture is heated to a temperature of about 90° C and a solution of magnesium chloride (14.28 grams; 0.15 mole) in water (100 ml.) is added thereto. The mixture is reheated to a temperature of about 80° C and is then allowed to cool to room temperature. The solid formed is recovered by filtration, is washed with water and is dried to yield the desired product of the empirical formula $Mg(C_6H_2OCH_3Cl_2CO_2)$ $(C_6H_3Cl_2OCH_2CO_2)$.

EXAMPLE 12

Preparation of a (Mixed Salt of Magnesium, 2-Methoxy-3,6-dichlorobenzoic Acid and 2,4-Dichlorobenzoic Acid of the Empirical Formula $Mg(C_6H_2OCH_3Cl_2CO_2)$ $(C_6H_3Cl_2CO_2)$ 2-Methoxy-3,6-dichlorobenzoic acid (33.15 grams; 85% assay; 0.15mole), 2,4-dichlorobenzoic acid (28.7 grams; 0.15 mole), sodium hydroxide (12 grams; 0.3 mole) and water (250 ml.) are charged into a glass reaction vessel equipped with a thermometer and mechanical stirrer. This mixture is heated to a temperature of about 90° C and a solution of magnesium chloride (14.28 grams; 0.15 mole) in water (100 ml.) is added thereto. The mixture is reheated to a temperature of about 80° C and is then allowed to cool to room temperature. The solid formed is recovered by filtration, is washed with water and is dried to yield the desired product of the empirical formula $Mg(C_6H_2OCH_3Cl_2CO_2)$ $(C_6H_3Cl_2CO_2)$.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites of the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and or oil to any desired concentration of active compound for application as sprays to the site of the weed infestation. The emulsifiers must commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 13

Preparation of a Dust

Product of Example 1 — 10
Powdered Talc — 90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of the weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5 to about 95 percent of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycloron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloroacetamide herbicides and as alpha-chloro-N,N-dimethylacetamide, CDEA, CDAA, alpha-chloro-N-isopropylacetamide, 2-chloro-N-isopropylacetanilide, 4-)chloroacetyl)morpholine, 1-)chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morning glory, bedstraw, ducksalad and naiad; biennials such as wild carrot, matricaria, wild barley, campion, chamomile,. burdock, mullein, round-leaved mallow, bull thistle, hounds-tongue, moth mullein, and purple star thistle; or perennials such as white cockle, perennial rye-grass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broad-leaf or grassy weeds. It is economically desirable to control the growth of such weeds without damaging beneficial plants or livestock The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre-and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and the test compounds formulated as aqueous emulsions of acetone solutions containing emulsifiers are sprayed at the desired concentrations on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of the compounds of this invention can be demonstrated by the foregoing procedure.

The herbicidal activity of the compounds of this invention can also be demonstrated by experiments carried out for the post-emergence control of a variety of weeds. In these experiments the compounds to be tested are formulated as aqueous emulsions and sprayed at the indicated dosage on the foliage of the various weed species that have attained a prescribed size. After spraying, the plants are placed in a greenhouse and watered daily or more frequently. Water is not applied to the foliage of the treated plants. The severity of the injury is determined 10 to 15 days after treatment and is rated on the scale of from 0 to 10 heretofore described The resistance to leaching of the compounds of the present invention was demonstrated in experiments wherein the migration of the compounds of this invention through soil was measured. In these experiments a plastic column was packed with soil which had previously been dried and passed through a 30 mesh screen. The column was packed to a soil depth of 3 inches. The test compounds were then applied to the soil surface in the form of a solid powder or xylene solution and water (284 ml.) equivalent to 6 inches of rainfall was then poured on top of the soil column in a single addition.

The column was allowed to stand for a period of 24 hours during which time the water slowly eluted from the bottom of the column was collected. The water eluant was then analyzed for the amount of test compound present.The aqueous solution was concentrated and hydrolyzed with 50 percent aqueous hydrochloric acid. The acidified solution was extracted with chloroform and analyzed by quantitative infra-red analysis as 2-methoxy-3,6-dichlorobenzoic acid. The stoichiometric conversion and subsequent analysis for the test compound in the water eluant indicated the amount of test compound which had passed through the soil column and is a measure of the degree of leaching of the test compound in soil. For comparative purposes, the identical leaching experiment was carried out using the dimethylamine salt of 2-methoxy-3,6-dichlorobenzoic acid. The result of these experiments is shown in the following table.

TABLE I

| Test Compound | Physical State on Application | Amount of Test Compound Applied to the Soil Expressed as Dicamba* | % Test Compound Present in the Water Eluant Based on Amount Applied to the Soil Expressed as Dicamba* |
|---|---|---|---|
| Product of Example 1 | Xylene Solution | 0.00296 grams | 22.8 |
| Dimethylamine Salt of 2-Methoxy-3,6-dichlorobenzoic Acid | Aqueous Solution | 0.00310 grams | 103.6 |

*Dicamba = 2-methoxy-3,6-dichlorobenzoic acid

I claim:
1. a herbicidal composition comprising an inert carrier, as an essential active ingredient, in a quantity toxic weeds, a mixed salt of magnesium having the empirical formula

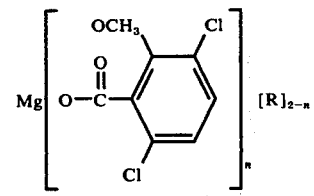

wherein R is an acid radical of from 7 to 20 carbon atoms and $n$ has an average value of from 0.5 to 1.5.
2. A method of controlling weeds which comprises contacting said weeds with a herbicidal composition of claim 1.

* * * * *